United States Patent [19]

Mascia

[11] Patent Number: 5,492,536
[45] Date of Patent: Feb. 20, 1996

[54] SAFELY DISPOSABLE SYRINGE

[76] Inventor: Michael F. Mascia, 4741 Columbia Rd., Ellicott City, Md. 21042

[21] Appl. No.: 823,315

[22] Filed: Jan. 21, 1992

[51] Int. Cl.$^6$ ..................................................... A61M 5/32
[52] U.S. Cl. .......................... 604/197; 604/198; 604/263
[58] Field of Search ..................................... 604/110, 192, 604/197, 198, 263, 187, 218; 128/919

[56] References Cited

U.S. PATENT DOCUMENTS

| | | |
|---|---|---|
| 2,674,246 | 4/1954 | Bower . |
| 4,425,120 | 1/1984 | Sampson et al. . |
| 4,631,057 | 12/1986 | Mitchell . |
| 4,723,943 | 2/1988 | Spencer . |
| 4,737,144 | 4/1988 | Choksi . |
| 4,738,663 | 4/1988 | Bogan . |
| 4,826,491 | 5/1989 | Schramm . |
| 4,846,796 | 7/1989 | Carrell et al. . |
| 4,863,434 | 9/1989 | Bayless ................................. 604/198 |
| 4,863,435 | 9/1989 | Sturman et al. ...................... 604/198 |
| 4,874,383 | 10/1989 | McNaughton . |
| 4,927,416 | 5/1990 | Tomkiel ................................ 604/198 |
| 4,929,241 | 5/1990 | Kulli ..................................... 604/263 |
| 4,932,947 | 6/1990 | Cardwell .............................. 604/198 |
| 4,943,282 | 7/1990 | Page et al. . |
| 4,950,249 | 8/1990 | Jagger et al. ......................... 604/192 |
| 5,026,353 | 6/1991 | Bartman .............................. 604/192 |
| 5,106,379 | 4/1992 | Leap ..................................... 604/198 |
| 5,135,510 | 8/1992 | Maszkiewicz et al. ............. 604/195 |
| 5,147,303 | 9/1992 | Martin .................................. 604/110 |
| 5,163,917 | 11/1992 | Huefner ............................... 604/198 |
| 5,176,656 | 1/1993 | Bayless ................................ 604/198 |
| 5,188,614 | 2/1993 | Hart ...................................... 604/197 |

FOREIGN PATENT DOCUMENTS 3825396   2/1990   Germany ............................. 604/198

Primary Examiner—C. Fred Rosenbaum
Assistant Examiner—Vanitha Alexander
Attorney, Agent, or Firm—Cesari and McKenna

[57] ABSTRACT

A hypodermic syringe with a protective sheath which is spring urged to cover the needle assembly and releaseably retained on the syringe barrel. The syringe comprises a syringe barrel with a needle assembly attached at one end and a plunger inserted in the other end for movement therein. The protective sheath is mounted over the syringe barrel for movement thereon. One end of a spring is attached to the syringe barrel and the other end is attached to the sheath. The spring is urged to push the sheath over the needle assembly creating a cone-shaped structure around the needle assembly. A hook on the flange engages the sheath and retains it in a retracted position, until released. A locking mechanism secures the sheath over the needle assembly once fully extended.

7 Claims, 2 Drawing Sheets

SAFELY DISPOSABLE SYRINGE

FIELD OF THE INVENTION

This invention relates generally to a disposable hypodermic syringe and more specifically to a hypodermic syringe with a protective sheath.

BACKGROUND OF THE INVENTION

A hypodermic syringe is used to inject fluids into or draw fluids from animal and human bodies. The syringe has a cylindrical barrel with a needle attached to one end and a plunger partly disposed in the other end. When purchased, all of the parts of a disposable syringe are sterile and arrive in sterile packaging. The needle itself is usually also shielded with a protective cap.

Typically, after inserting the syringe needle into the patient for an injection, the user adjusts his grip so that his second and third fingers fit under a flange on the syringe barrel and his thumb rests on top of the plunger. The plunger is then pressed into the syringe barrel by the user's thumb while the second and third fingers press against the flange. The resulting forward movement of the plunger forces medicine through the needle and into the patient.

Contamination of a hypodermic needle, which results from contact with human or animal tissues, blood, or other bodily fluids, may be dangerous when it contains infectious organisms. Health care workers have developed serious infections from accidental punctures or scrapes, collectively termed "needle sticks".

After use of a syringe, the original protective cap may be replaced to eliminate the risk of an accidental needle stick. However, this has proven to be hazardous. To cover the needle with a protective cap, one hand must hold the syringe with one hand while using the other hand to place the protective cap over the needle. If the user fails to insert the needle into the cap, he may accidentally puncture his other hand.

In emergencies, the likelihood of suffering a needle stick is even greater. The health care worker is faced with two options, either to quickly attempt to shield the needle with a protective cap, increasing the risk of a needle stick, or to leave the contaminated needle exposed as a threat to other workers in the environment. Neither alternative is desirable. Indeed, recognizing the risk recapping imposes, some health care facilities recommend that their workers not attempt to recap contaminated needles.

Disposal containers for syringes, used by some health care workers, have achieved minimal success in eliminating the risk of a needle stick. As with protective caps, disposal containers are often lost or are simply out of reach when needed. Additionally, the use of disposal containers has proven to be cumbersome.

Manually operated protective sheaths, developed to eliminate the risks of accidental puncture, have also been proposed. Typically, these protective sheaths, which are cylindrical in shape, are slidably mounted over the syringe barrel. As with the other protective arrangements discussed above, both hands are needed. While holding the syringe in one hand, the user's other hand must reach for the sheath and then slidably engage and lock the sheath over the needle. If the user is hurried or careless when reaching for the sheath, he may incur a needle stick.

Accordingly, it is a principal object of this invention to provide a hypodermic syringe with a protective sheath which can be readily deployed with one hand.

Another object of the invention is to provide a syringe with a protective sheath that effectively prevents needle sticks when it is deployed.

A further object is to provide a syringe with a protective sheath that may be in its deployed position to maintain protection from needle sticks during subsequent handling of the syringe.

Another object of this invention is to provide a syringe with a protective sheath that permits use of measurement indicia on the syringe barrel.

SUMMARY OF THE INVENTION

In accordance with the invention, a cylindrical protective sheath is slidably mounted on the syringe barrel and is spring-urged to cover the needle assembly. A latching arrangement retains the sheath on the syringe barrel and when the latch is released, the spring moves the sheath forward to deploy the sheath over the needle assembly. The sheath automatically locks in this position. Thus, once the protective sheath is deployed, an accidental needle stick is almost impossible. The entire shielding operation can be accomplished with only one hand, thus eliminating the dangers attendant on two-handed operation.

More specifically, in the preferred embodiment of the invention one or more hooks, connected to the underside of the flange on the syringe barrel, engage an annular rib on the protective sheath to latch the sheath in its undeployed position on the syringe barrel. Upon completion of an injection, the user may release the sheath merely by increasing the force applied by the thumb and fingers. This bends the flange backwardly, releasing the hooks from the sheath and thus unlatching the sheath for forward movement.

Preferably, the forward end of the sheath is formed as a series of fingers. A slotted base near the forward end of the syringe barrel guides these fingers around the needle assembly to form a rigid, cone-shaped structure around the needle when the sheath is deployed. At the same time the rearward end of the sheath engages with the base to lock the sheath, in place over the needle. An optional protective cap may then be placed over the converged fingers for added protection. However, with the needle end covered by the sheath fingers, this operation poses no risk.

BRIEF DESCRIPTION OF THE DRAWINGS

The above and further features and advantages of the invention may be better understood by referring to the following description in conjunction with the accompanying drawings, in which.

DETAILED DESCRIPTION OF ILLUSTRATIVE EMBODIMENTS

Figure 1:
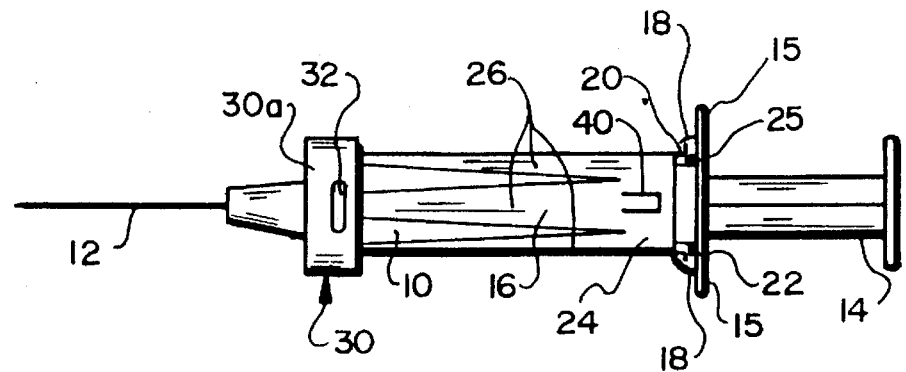
FIG. 1 is a side view of a syringe embodied in accordance with the invention with the sheath in a retracted position.

FIG. 1 illustrates a hypodermic syringe having a cylindrical syringe barrel 10 containing a pharmaceutical (not shown) to be injected into a patient. A needle 12 is connected to the forward end of the barrel 10 and the forward end of a plunger 14 is disposed within the rearward portion of the barrel.

As is well known, the user dispenses the pharmaceutical from the syringe by placing the index and middle fingers behind a flange 15 at the rearward end of the barrel 10 and forcing the plunger 20 forward with the thumb of the same hand. The needle 12 is then retracted from the patient's body. The needle is contaminated in the injection process, making safe disposal a problem with prior syringes.

Figure 2:
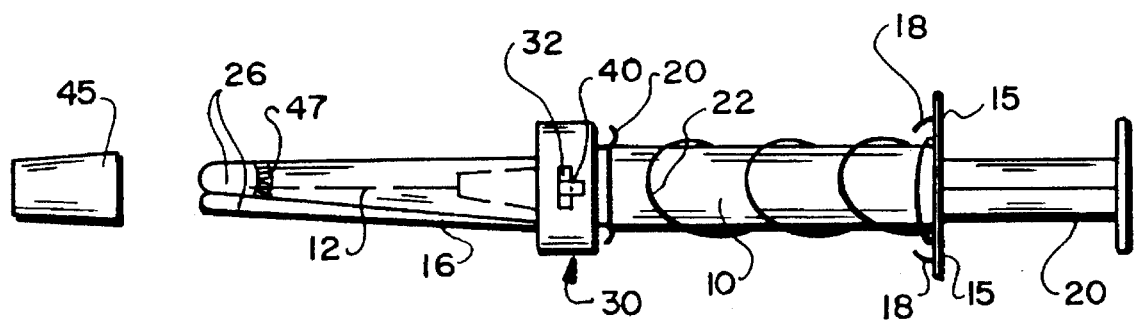
FIG. 2 is a side view of the syringe of FIG. 1 with the sheath deployed to shield the syringe needle.

The syringe also includes a needle-sheathing arrangement embodying the principles of the present invention. A generally cylindrical protective sheath 16 surrounds the syringe barrel 10 when the sheath is in the retracted position as shown in FIG. 1. The sheath 16 is retained in that position by a latch comprising one or more hooks 18, integral with the flange 15, and a flange 20 at the rearward end of the sheath 16. When the latch is released, a coiled spring 22, disposed between the flange 20 and the flange 15, urges the sheath 16 forward, toward its deployed position, where it covers the needle 12, as shown in FIG. 2.

More specifically, in FIG. 1, the sheath 16, mounted on the syringe barrel 10 for movement thereon, is detachably held in a retracted position, until released by the user to shield the needle 12. It includes an annular band 24 between the flange 20 and a set of fingers 26. The fingers 26 extend partly through arcuate slots 28 in a drumlike base 30 (FIGS. 1 and 3) that is secured at the forward end of the syringe barrel 10. Typically, the sheath 16 is made from a clear material, such as clear plastic, so that volumetric indicia on the syringe barrel 10 will not be obscured by the sheath.

Figure 3:
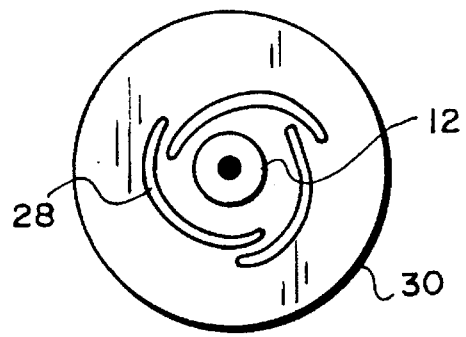
FIG. 3 is an enlarged end view of the slotted base of the syringe of FIG. 1.

The fingers 26 preferably have a curvature similar to that of the slots 28. The slots 28 are spaced radially inward with respect to the band 24. Accordingly, when the sheath 16 is released and urged forward over the needle 12, the fingers 26 are guided inward at an angle determined by the distance between the slots 28 and base 30 and the difference in their radii from the axis of the syringe. As a result, the fingers converge to a cone around the needle 12, as shown in FIG. 2. Moreover, as shown in FIG. 3, the slots 28 overlap and are so oriented that the fingers 26 are twisted and overlapped when the sheath 16 moves forward. The resulting cone is therefore both closed and stiff and the needle 12 is thus completely and securely surrounded by the fingers.

To deploy the sheath 12, a user pulls back on the flange 15 with greater force than that used during an injection. This deforms the flange 15, causing the hooks 18 to bend outwardly and to release from the rib flange 20. The flange 15 is sufficiently thick that additional force, beyond the amount normally needed to inject medicine or withdraw a needle from a patient's body, is needed to deform the flange.

The base 30 also has an aperture 32 in its annular side wall 30a. As shown in FIG. 2, a spring-like detent 40, protruding from the sheath band 24, moves into the aperture 32 when the sheath 16 is deployed, thereby locking the sheath in its forward position.

As a further precautionary measure, an optional protective cap 45 (FIG. 2) may be placed over the converged fingers 26 to further secure the needle assembly 12. To retain the cap 45 on the fingers, ridge 47 may be formed on the outer surface of one or more of the fingers 45, near the forward end thereof. The ridge 47 engages in a groove (not shown) inside the cap 45.

Figure 4:
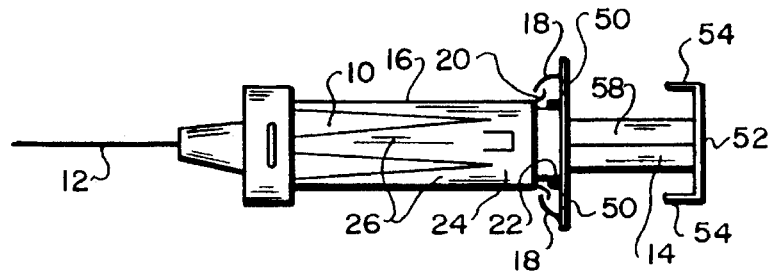
FIG. 4 is a side view of another embodiment of the syringe in accordance with the invention with the sheath in a retracted position.
Figure 5:
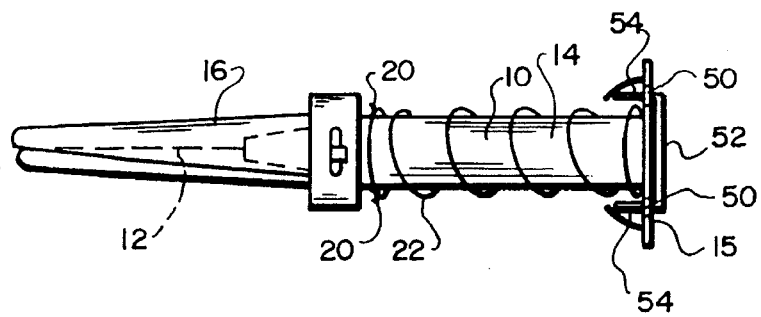
FIG. 5 is a side view of the syringe of FIG. 4 with the sheath in its deployed position.
Figure 6:
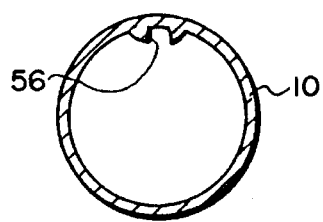
FIG. 6 is an enlarged sectional view of the barrel of the syringe of FIG. 4.

FIG. 4 shows an alternative embodiment of the invention. Components labelled with like reference numerals in FIGS. 1 and 4 are identical. The flange 15 is made of a relatively rigid material and has a pair of apertures 50 extending through it. The plunger 14 has a plunger head 52 with forwardly extending projections 54. When the plunger 14 is forced fully forward, the projections 54 pass through the apertures 50 and engage the hooks 18. As shown in FIG. 5, this bends the hooks outwardly to release the sheath 16 for forward movement to cover the needle 12. To ensure alignment of the projections 54 with the apertures 50, the syringe barrel 10 may be provided with an internal channel 56 (FIG. 6) that compensates with a longitudinal key 58 (FIG. 4) on the plunger 14.

FIG. 5 illustrates the syringe of FIG. 4 with the plunger 14 pushed into the syringe barrel 10 and the projections 54 engaging the hooks 18. With the hooks thus disengaged from the flange 20, the spring 22 has pushed the sheath 16 forwardly to cover needle 12.

The foregoing description has been limited to specific illustrative embodiments of this invention. It will be apparent, however, that variations and modifications may be made to the invention, with the attainment of some or all of its advantages. Therefore, it is the object of the appended claims to cover all such variations and modifications as come within the true spirit and scope of the invention.

I claim:

1. A syringe comprising:
   a syringe barrel open at one end and having a needle assembly at the other end;
   a flange formed near the open end of the syringe barrel;
   a plunger disposed in the syringe barrel for movement therein;
   a sheath slidably mounted over the syringe barrel, the sheath having a plurality of longitudinally-extending fingers at one end capable of bending inwardly together to form a generally cone-shaped closed covering for the needle assembly and having a generally cylindrical shape at the other end;
   means for biasing the sheath to an extended position over the needle assembly;
   retaining means for detachably engaging said other end of the sheath to retain the sheath in a retracted position over the syringe barrel; and
   a base attached to the syringe barrel at the needle assembly end, said base having a plurality of overlapping, radially displaced slots through which the fingers pass;
   whereby, when said retaining means is detached from said sheath, said biasing means moves said sheath forward to said extended position and said slots guide said fingers around said needle assembly and bend them inwardly.

2. A syringe as in claim 1 wherein the radially displaced slots are located within a circumference of the base that is smaller than the circumference of the syringe barrel.

3. A syringe as in claim 1 further comprising a protective cap which fits over the collapsed fingers.

4. A syringe as in claim 1 wherein the retaining means comprises an annular rib on the cylindrical end of the sheath which engages at least one hook assembly formed on the flange, the hooks being released from the rib when the flange is deformed rearwardly, away from the needle assembly.

5. A syringe as in claim 1 including means for locking the sheath in its extended position over the needle assembly, said locking means comprising at least one detent formed on the cylindrical end of the sheath which is capable of engaging at least one mating slot on the base.

6. A hypodermic syringe comprising:

a syringe barrel that is open at one end and having a needle assembly at the other end;

a flange with at least one aperture connected near the open end of the syringe barrel;

a plunger disposed in the syringe barrel for movement therein;

a plunger head connected to the plunger with at least one projection extending in the direction of the needle assembly and aligned with in the aperture;

a sheath slidably mounted over the syringe barrel, the sheath having a plurality of fingers at one end bendable inwardly to form a generally cone-shaped closed covering for the needle assembly and having a generally cylindrical shape at the other end;

means for biasing the sheath to an extended position over the needle assembly;

retaining means for detachably engaging the cylindrical end of the sheath to retain the sheath in a retracted position over the syringe barrel, means for locking the sheath in its extended position over the needle assembly; and means for guiding the fingers around the needle assembly, said guiding means comprising a plurality of overlapping radially displaced slots in the base through which the fingers pass and which bend the fingers inwardly when the sheath moves to the extended position.

7. A hypodermic syringe as in claim 6 wherein the radially displaced slots are located within a circumference of the base that is smaller than the circumference of the syringe barrel.

* * * * *